(12) United States Patent
Needham et al.

(10) Patent No.: US 7,060,067 B2
(45) Date of Patent: Jun. 13, 2006

(54) SYSTEMS, INSTRUMENTATION AND TECHNIQUES FOR RETAINING FASTENERS RELATIVE TO A BONE PLATE

(75) Inventors: Dusty Anna Needham, Eads, TN (US); Bradley J. Coates, Rossville, TN (US); Kenneth S Shipp, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 686 days.

(21) Appl. No.: 10/222,570

(22) Filed: Aug. 16, 2002

(65) Prior Publication Data

US 2004/0034352 A1    Feb. 19, 2004

(51) Int. Cl.
*A61B 17/70*    (2006.01)
(52) U.S. Cl. .............................. 606/61; 606/70; 606/72
(58) Field of Classification Search .................. 606/61, 606/69, 70, 71, 72
See application file for complete search history.

(56) References Cited

U.S. PATENT DOCUMENTS

| 4,796,612 | A | 1/1989 | Reese |
| 5,057,111 | A | 10/1991 | Park |
| 5,269,784 | A | 12/1993 | Mast |
| 5,388,619 | A | 2/1995 | Ghawi |
| 5,951,558 | A | 9/1999 | Fiz |
| 6,022,351 | A | * | 2/2000 | Bremer et al. ................ 606/72 |
| 6,139,550 | A | 10/2000 | Michelson |
| 6,235,034 | B1 | 5/2001 | Bray |
| 6,261,291 | B1 | 7/2001 | Talaber et al. |
| 6,331,179 | B1 | 12/2001 | Freid et al. |
| 6,413,259 | B1 | 7/2002 | Lyons et al. |
| 6,485,493 | B1 * | 11/2002 | Bremer ........................ 606/70 |

FOREIGN PATENT DOCUMENTS

| DE | 198 32 798 C1 | 11/1999 |
| EP | 0 242 842 A2 | 4/1987 |
| EP | 0 242 842 B1 | 3/1993 |
| EP | 1 169 971 A2 | 1/2002 |
| WO | WO 00/49949 A1 | 8/2000 |
| WO | WO 02/09602 A1 | 2/2002 |

* cited by examiner

*Primary Examiner*—David O. Reip
(74) *Attorney, Agent, or Firm*—Krieg DeVault LLP

(57) ABSTRACT

Retaining mechanisms are attachable to a bone plate to retain one or more bone engaging fasteners relative to the bone plate. The retaining mechanisms include a retaining element engaged to an attachment element. One or both of the retaining element and the attachment element are moveable relative to the plate to position and/or maintain the retaining element in contact with one or more bone engaging fasteners.

18 Claims, 8 Drawing Sheets

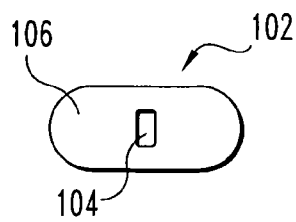
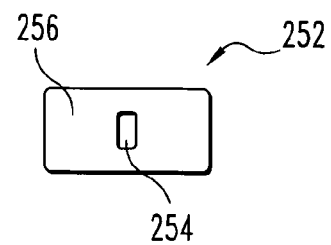
*Fig. 6*  *Fig. 7*
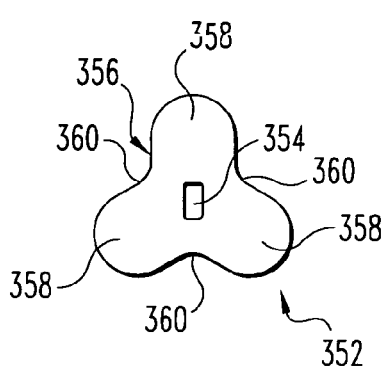
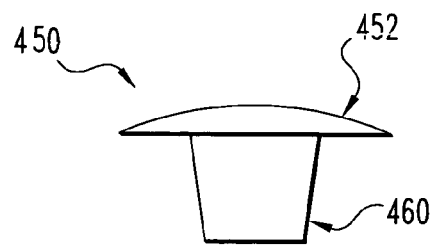
*Fig. 8*  *Fig. 9*
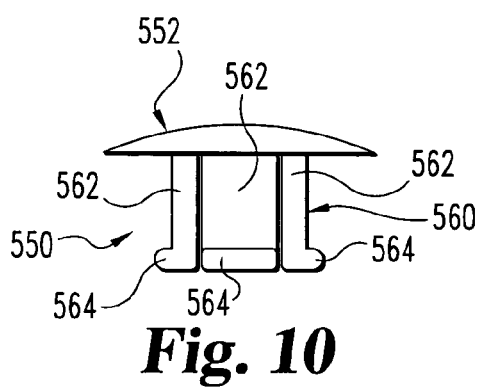
*Fig. 10*
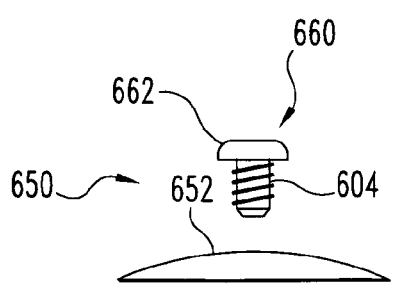
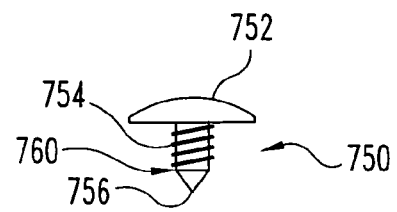
*Fig. 11*  *Fig. 12*

US 7,060,067 B2

SYSTEMS, INSTRUMENTATION AND TECHNIQUES FOR RETAINING FASTENERS RELATIVE TO A BONE PLATE

BACKGROUND

Bone plates can be engaged to adjacent bony portions of a bone or of a bony segment to stabilize the bone portions. Fasteners can be used to engage the bone plate to the bony portions. To prevent the fasteners from backing out of the plate, various set screw type retaining devices have been developed for engagement to the plate adjacent to or around the bone fasteners. Other retaining devices include an arm integrally formed with the plate and bendable to extend over a fastener in a plate hole. These retaining devices block the fasteners to prevent them from backing out of the plate.

There can be some problems associated with prior retaining devices. For example, in prior retaining devices, the head of one or more of the bone plate fasteners may interfere with the proper positioning and alignment of the retaining device relative to the fastener. Prior retaining devices may not be positionable in contact with or maintained in contact with one or more of the fasteners if the fasteners move relative to the plate, or if multiple fasteners associate with the retaining device are not at the same position relative to the plate. Also, prior retaining devices can be difficult to handle, install and/or manipulate.

SUMMARY

According to one aspect, there is provided a retaining mechanism attachable to a bone plate that is resiliently deformable to contact and/or maintain contact with one or more bone engaging fasteners.

According to another aspect, there is provided a retaining mechanism having a retaining element axially loadable along an attachment element attached to the bone plate to contact one or more bone engaging fasteners.

According to another aspect, there is provided a mechanism for retaining at least one bone engaging fastener relative to a bone plate. The retaining mechanism includes an attachment portion attachable to the bone plate. The attachment portion includes an attachment element having a retaining element coupled thereto. When the attachment portion is attached to the bone plate the attachment element extends proximally from the bone plate, and the retaining element is moveable along the attachment element from a first position substantially spaced from the bone plate to a second position in contact with the at least one bone engaging fastener.

According to a further aspect, there is provided a mechanism for retaining at least one bone engaging fastener relative to a bone plate. The retaining mechanism include an attachment portion attachable to the bone plate and a proximally extending attachment element. A retaining element is coupled to the attachment element. The attachment element is movable relative to the bone plate to assume any one of a plurality of positions relative thereto when the attachment portion is attached to the bone plate and the retaining element is in contact with the at least one bone engaging fastener.

According to one aspect, a retaining mechanism for retaining at least one bone engaging fastener relative to a bone plate is provided. The retaining mechanism includes an attachment portion having an abutment member positionable against a distal surface of the bone plate and an attachment element extending proximally from the abutment member through the bone plate. A retaining element is movable distally along the attachment element into contact with the at least one bone engaging fastener.

According to another aspect, there is provided a retaining mechanism for retaining at least two bone engaging fasteners relative to a bone plate. The retaining mechanism includes an attachment portion attachable to the bone plate and a retaining element coupled to the attachment portion. The retaining element is contactable with each of the at least two bone engaging fasteners when the attachment portion is attached to the bone plate. The retaining element and the attachment portion are flexible to maintain the retaining element in contact with each of the at least two bone engaging fasteners.

According to another aspect, a system is provided including a bone plate having at least one hole and at least one receptacle adjacent the at least one hole, a bone engaging fastener positioned in the at least one hole, and a retaining mechanism positioned in the receptacle. The retaining mechanism includes a retaining element in contact with at least one of the bone plate and the at least one bone engaging fastener. The retaining mechanism includes an abutment member in contact with a distal surface of the bone plate and coupled to the retaining element. The retaining element and the abutment member are movable toward one another to apply a clamping force to the bone plate.

According to one aspect, there is provided a system including a bone plate having at least one hole and at least one receptacle adjacent the at least one hole, a bone engaging fastener positioned in the at least one hole, and a retaining mechanism positioned in said receptacle and including a retaining element in contact with the at least one bone engaging fastener, and an abutment member in contact with a distal surface of the bone plate. The bone engaging fastener extends through a passage in the abutment member.

According to another aspect, there is provided a system including a bone plate having at least one hole therethrough and at least one receptacle adjacent the at least one hole, a bone engaging fastener positioned in the hole, and a retaining mechanism in the receptacle including a retaining element axially loadable onto the plate in contact with the bone engaging fastener. The retaining element is resiliently deformable in response to movement of the at least one bone engaging fastener relative to the bone plate to maintain contact between the retaining element and the bone engaging fastener.

According to another aspect, there is provided a system including a bone plate having two adjacent holes therethrough and at least one receptacle adjacent the two holes, a bone engaging fastener positioned in each hole, and a retaining mechanism positioned in the receptacle. The retaining mechanism includes an attachment portion attachable to the bone plate and a retaining element engaged to the attachment portion. The attachment portion is resiliently deformable to assume any one of a plurality of orientations relative to the bone plate so that the retaining element maintains contact with each of the bone engaging fasteners.

According to a further aspect, a method for securing a bone plate to a spinal column segment is provided. The method includes engaging the bone plate to first and second vertebrae of the spinal column segment with a pair of bone engaging fasteners in at least one of the first and second vertebrae; attaching a retaining element to the bone plate adjacent the pair of bone engaging fasteners; resiliently deforming the retaining element as the retaining element is placed into contact with the pair of bone engaging fasteners;

and moving the pair of bone engaging fasteners relative to the plate while the retaining mechanism maintains contact therewith.

According to another aspect, a method for securing a bone plate to a spinal column segment is provided. The method includes engaging the bone plate to first and second vertebrae of the spinal column segment with at least one bone engaging fastener in each of the first and second vertebrae; advancing a retaining element distally along an attachment element extending proximally from the bone plate; and deforming the attachment element to position the retaining element in contact with the at least one bone engaging fastener.

These and other aspects will also be apparent from the following description.

BRIEF DESCRIPTION OF THE FIGURES

FIG. 6 is a plan view of another embodiment retaining element.

FIG. 7 is a plan view of another embodiment retaining element.

FIG. 8 is a plan view of another embodiment retaining element.

FIG. 9 is an elevation view of another embodiment retaining mechanism.

FIG. 10 is an elevation view of another embodiment retaining mechanism.

FIG. 11 is en elevation view of another embodiment retaining mechanism.

FIG. 12 is en elevation view of another embodiment retaining mechanism.

DESCRIPTION OF THE ILLUSTRATED EMBODIMENTS

Figure 1:
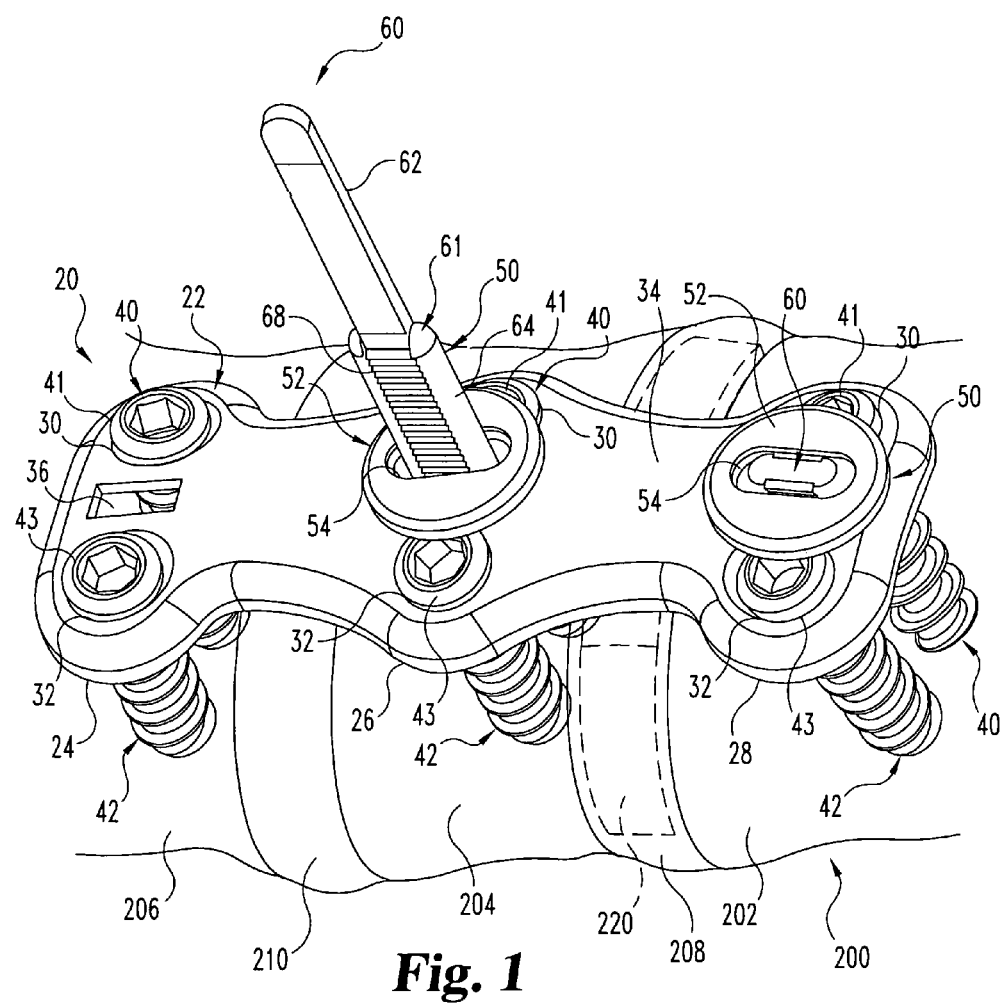
FIG. 1 is a perspective view of a plating system attached to a bony segment.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated herein are contemplated as would normally occur to one skilled in the art to which the invention relates.

Bone plates are engageable to bony segments with one or more bone engaging fasteners. The present invention provides one or more retaining mechanisms that can be attached to a bone plate in contact with the one or more bone engaging fasteners that engage to the plate to the bony segment. The retaining mechanisms prevent or resist backout of the one or more bone engaging fasteners relative to the plate.

Figure 2:
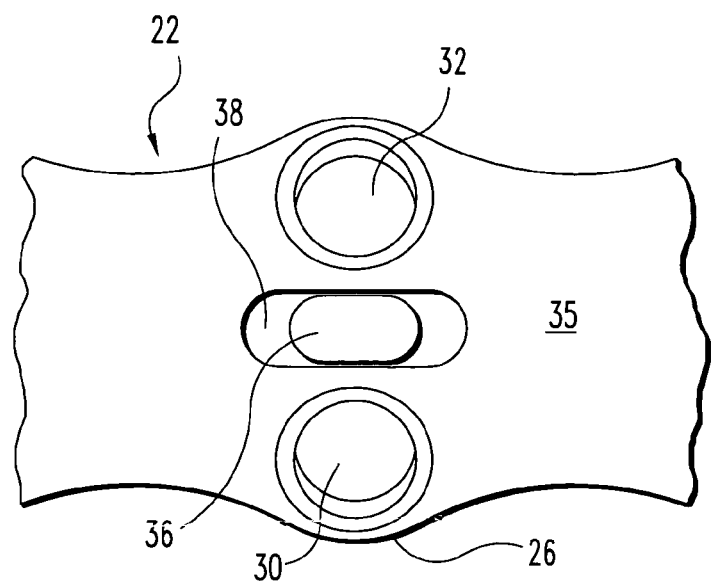
FIG. 2 is a bottom view of a portion of a plate comprising a portion of the plating system of FIG. 1.

Referring to FIG. 1, plating system 20 includes a bone plate 22, a number of bone engaging fasteners 40, 42 and retaining mechanisms 50. Bone plate 22 includes a plurality of nodes 24, 26, 28 therealong. Each node 24, 26, 28 can be provided with a first hole 30 and an adjacent second hole 32 extending between and opening at a proximal surface 34 and a distal surface 35 (FIG. 2) of plate 22. Positioned adjacent each of the plates holes 30, 32 is a receptacle 36 for attachment of retaining mechanisms 50 to bone plate 22.

Bone engaging fasteners 40, 42 are positionable in respective ones of the holes holes 30, 32 to secure plate 22 to bony structure under plate 22. Holes 30, 32 can be circular, or elongated in the form of a slot. Bone engaging fasteners 40, 42 can be any bone engaging fastener, such as a screw, anchor, bolt, nail, or other fastener capable of securing plate 22 to bony structure. When positioned in holes 30 and 32, heads 41, 43 of bone engaging fasteners 40, 42 can be fixed, pivotal, translatable or otherwise movable in holes 30, 32. It is contemplated that heads 41, 43 can extend at least slightly proximally from proximal surface 34 for contact with retaining mechanism 50. It is also contemplated that one or more of the heads 41, 43 could be recessed below proximal surface 34.

Retaining mechanism 50 includes a retaining element 52 that can contact heads 41, 43 of fasteners 40, 42, respectively, when fasteners 40, 42 are positioned in holes 30, 32 and retaining mechanism 50 is attached to plate 22 in receptacle 36. Retaining mechanism 50 prevents and/or limits the backout of fasteners 40, 42 relative to plate 22.

Figure 3:
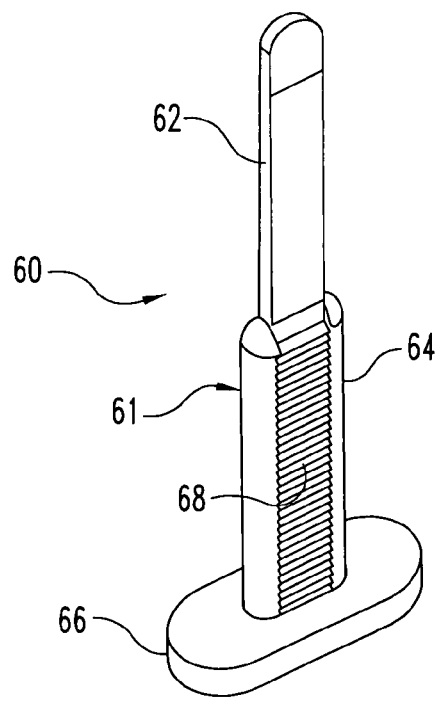
FIG. 3 is a perspective view of an attachment portion of a retaining mechanism of the plating system of FIG. 1

Retaining mechanism 50 includes retaining element 52 coupled to an attachment portion 60. Attachment portion 60 is attachable to plate 22. As shown in further detail in FIG. 3, attachment portion 60 includes an attachment element 61 extending proximally from an abutment member 66. Attachment element 61 includes a proximal portion 62 and a retaining element engagement portion 64 adjacent abutment member 66. Retaining element 52 is engageable to engagement portion 64 at any one of a number of positions therealong to secure retaining element 52 to plate 22.

It is contemplated that attachment element 61 can be movable relative to plate 22 so that retaining element 52 can be positioned in and maintained in contact with the heads of bone engaging fasteners 40, 42. In one embodiment, attachment portion 61 is made from a resiliently deformable material having sufficient flexibility to bend, twist or otherwise move relative to plate 22 in receptacle 36 to assume any one of an infinite number of orientations with respect to plate 22. It is also contemplated that retaining element 52 can move by any one or combination of pivoting relative to attachment element 61, axially displacing relative to attachment element 61, rotating relative to attachment element 61, and flexing relative to attachment element 61.

Figure 4:
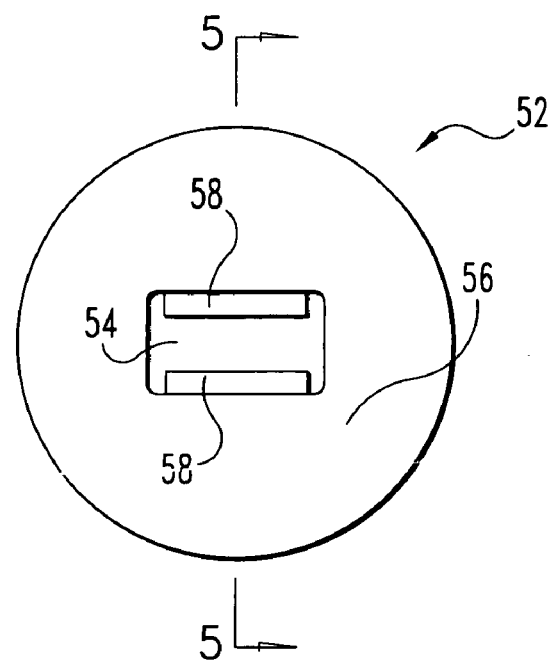
FIG. 4 is a plan view of a retaining element comprising a portion of the retaining mechanism of the plating system of FIG. 1.
Figure 5:
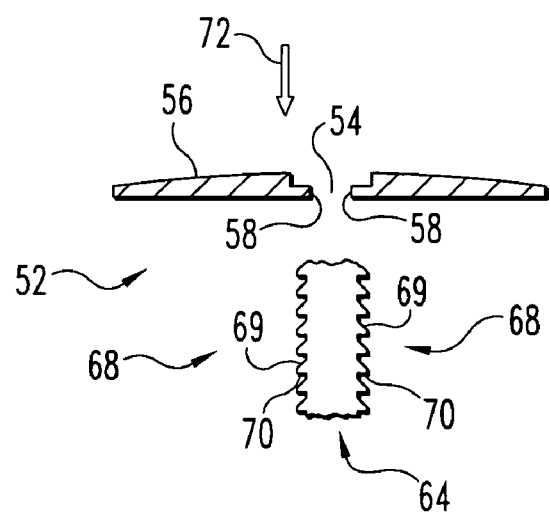
FIG. 5 is a section view through line 5—5 of FIG. 4 with a portion of an attachment element of the retaining mechanism adjacent thereto.

Attachment portion 60 can be attached to plate 22 by positioning attachment element 61 through receptacle 36 of bone plate 22 with abutment member 66 positioned adjacent to or against distal surface 35. Attachment element 61 can be provided with a ratchet surface 68 along one or both sides of engagement portion 64. As shown in FIGS. 4 and 5, retaining element 52 includes a body 56 having a central opening 54 formed therethrough sized to receive attachment element 61.

Retaining element 52 can be provided with a pair of opposing locking members 58 extending into central opening 54 to engage ratchet surfaces 68 as retaining element 52 is moved along attachment element 61. As shown in FIG. 5, it is contemplated that locking members 58 can compress ratchet surfaces 68 as they ride along the adjacent ones of sloped surfaces 69. As locking members 58 move distally past one of the sloped surfaces 69, they are positioned in abutting contact with corresponding ones of the locking surfaces 70. Locking members 58 abut the respective locking surfaces 70, which prevent or substantially prevent proximal movement of retaining element 52 along attachment element 61.

In one embodiment, retaining element 52 is fabricated from a plastic material having a rigidity that is greater than that of the plastic material comprising attachment portion 60. Thus, locking members 58 can deform the ratchet surfaces 68 as locking members 58 are distally advanced along sloped surfaces 69. However, if it is attempted to move retaining element 52 proximally along attachment element 61, the more rigid locking members 58 will not deform or bend distally to move past the engaged locking surfaces 70 without the exertion of significant force. In one particular embodiment, retaining element 52 is made from acetal and attachment portion 60 is made from polypropylene. Other embodiments contemplate other materials as discussed herein.

In the illustrated embodiment, attachment element 61 has a rectangular cross-section, and is sized for receipt through receptacle 36, which also has a rectangular shape. Abutment member 66 is positioned against or adjacent to distal surface 35. To minimize the distal extent of abutment member 66, a recess 38 can be provided in distal surface 35 to receive abutment member 66. Recess 38 can also prevent abutment member 66 from rotating relative to plate 22. In the illustrated embodiment, recess 38 and abutment member 66 have an oval shape, although other shapes are also contemplated, including circular, square, rectangular, polygonal shape, and any other suitable shape for contacting distal surface 35.

Prior to positioning plate 22 to the surgical site, attachment element 61 of attachment portion 60 can be inserted through one or all of the receptacles 36 of bone plate 22 with abutment member 66 in contact with distal surface 35. Abutment member 66 can be positioned in distal surface formed in recess 38 if a recess is so provided. Retaining element 52 can be preloaded over the proximal end of attachment element 61 at a first position space from the bone plate. The bone plate can be positioned on and engaged to the bony segment with bone engaging fasteners. A flexible attachment portion 60 allows retaining element 52 to be easily moved and held out of the way during insertion of the bone engaging fasteners. Retaining element 52 can then be advanced distally into contact with the heads 41, 43 of bone engaging fasteners 40, 42 in holes 30, 32, respectively. As shown in FIG. 1, once retaining element 52 is seated in contact with heads 41, 43, the portion of attachment element 61 extending proximally from retaining element 52 can be removed by cutting, tearing, bending or the like to minimize the proximal extent of retaining mechanism 50 relative to plate 22.

Retaining element 52 can have sufficient flexibility to be resiliently deformable when placed in contact with heads 41, 43 of bone engaging fasteners 40, 42. For example, heads 41, 43 may be at mismatched positions relative to plate 22 upon initial insertion and/or through post-operative movement. The resiliently deformable retaining element 52 can bend or flex about its body 56 when pushed into contact with the mismatched bone engaging fasteners. Alternatively or additionally, retaining element 52 can move relative to attachment element 61 to contact or maintain contact with mismatched heads 41, 43 of bone engaging fasteners 40, 42. Alternatively or additionally, attachment element 61 can be provided with sufficient flexibility to resiliently deform relative to plate 22 as retaining element 52 is placed into contact or maintained in contact with each of the heads of the mismatched bone engaging fasteners.

It is also contemplated that retaining element 52 and/or attachment element 61 can be provided with sufficient flexibility to resiliently deform in response to the movement of one or both of the fasteners 40, 42 while remaining in contact with each of the fasteners 40, 42. The proximal movement of fastener 40 and/or fastener 42 can be limited when, for example, the resistance to further flexing, deformation and/or movement provided by retaining element 52 and/or attachment element 61 exceeds the backout force of the bone engaging fastener.

Retaining mechanism 50 can be used with bone plates and fasteners in which pivoting and/or translation of the fasteners relative to the plate is desirable while preventing or limiting the back out of the fasteners from the plate. Retaining mechanism 50 can also be used with bone plates and fasteners in which the fasteners are fixed relative to the plate to prevent or limit the back out of the fixed fasteners from the plate. The same retaining mechanism 50, or multiple retaining mechanisms 50, can also be employed with any one or combination of fixed, pivotal, and translatable fasteners in the same bone plate. One or both of the retaining element 52 and attachment portion 60 can be made from plastic material having sufficient flexibility to deform or move into and to maintain contact with the bone engaging fasteners when the retaining element 52 is attached to the bone plate. Embodiments of the invention also contemplate that one or both of the retaining element 52 and attachment portion 60 can be made from metals or metal alloy, including titanium and stainless steel, or other suitable biocompatible material.

In FIG. 1 retaining element 52 has a circular shape in plan view. Other shapes are also contemplated. For example, in FIG. 6 retaining element 102 has a body 106 with an oval or racetrack shape and a central opening 104 therethrough. In FIG. 7 retaining element 252 has a body 256 with a rectangular or square shape and a central opening 254 therethrough. In FIG. 8 retaining element 352 has a body 356 with a central opening 354. Body 356 has a pinwheel shape with a number of extensions 358 for contacting the heads of the bone engaging fasteners, and radiused cutouts 360 between adjacent ones of the extensions 358. Also contemplated are triangular, star, cross, polygonal, and other shapes suitable for contacting one or more bone engaging fasteners when the retaining element is attached to the bone plate.

Various forms for attachment portion 60 are also contemplated. For example, in FIG. 9 there is a retaining mechanism 450 having a retaining element 452 and an attachment portion 460. Attachment portion 460 can be integrally formed with retaining element 452, or part of a separate member that extends through a central opening through retaining element 452. Attachment portion 460 can be tapered for a force fit in the receptacle of the plate to attach retaining element 452 to the bone plate in contact with one or more bone engaging fasteners.

In another example shown in FIG. 10, there is a retaining mechanism 550 having a retaining element 552 and an attachment portion 560. Attachment portion 560 can be integrally formed with retaining element 552, or part of a separate member that extends through a central opening through retaining element 552. Attachment portion 560 can include a number of fingers 562 extending distally from retaining element 552 separated by spaces or gaps therebetween. Fingers 562 can flex inwardly as retaining mechanism is inserted through the plate receptacle, and return toward their pre-insertion configuration once inserted through the plate receptacle. Each of the fingers 562 includes a protrusion 564 extending radially outwardly therefrom to contact a distal surface of the plate to attach retaining mechanism 550 thereto in contact with one or more bone engaging fasteners.

In another example shown in FIG. 11, there is a retaining mechanism 650 having a retaining element 652 and an attachment portion 660. Attachment portion 660 has a shaft 664 with a thread pattern therealong to engage the bone plate in the receptacle. Attachment portion 660 can be a separate set screw received in an opening through retaining element 652, or can be integrally formed with retaining element 652 such that the entire retaining mechanism is rotated to threadingly engage the bone plate until retaining element 652 contacts the one or more bone engaging fasteners.

In another example shown in FIG. 12, there is a retaining mechanism 750 having a retaining element 752 and an attachment portion 760. Attachment portion 760 includes a shaft 754 with a thread pattern therealong to engage the bone plate in the receptacle. Shaft 754 can be integral with retaining element 752, and such that the entire retaining mechanism 750 is rotated to threadingly engage the bone plate until retaining element 752 contacts the one or more bone engaging fasteners. Shaft 754 can be provided with a pointed or sharp leading end 756 to penetrate bony structure underlying the plate. Other embodiments contemplate shaft 754 with a blunt leading end 756.

It is contemplated that retaining mechanisms described herein may include an attachment portion integrally formed with the retaining element. It is contemplated that the attachment portion of the retaining mechanisms can be threaded for engagement with the receptacle in the plate; press-fit into frictional engagement with the receptacle; or welded, fused, or glued to the plate in the receptacle or to another plate surface. It is also contemplated the attachment portion and retaining element can be configured to clamp the bone engaging fasteners by pressing against a distal surface of the plate and against a proximal surface of the plate and/or the proximal ends of the bone engaging fasteners.

In some applications, it is contemplated that the bone plate will be used to stabilize a spinal column segment 200. For example, in FIG. 1 there is shown a cervical spinal column segment 200 with vertebrae 202, 204 and 206. Disc space 208 is located between vertebrae 202, 204, and disc space 210 is located between vertebrae 204, 206. An implant, such as implant 220 in disc space 208, can be positioned in one or both of the spinal disc spaces 208, 210. Plate 22 can then be attached to two or more of the vertebrae to stabilize spinal column segment 200.

It is contemplated that implant 220 could be a bone graft, interbody fusion device, artificial disc device, or other interbody implant. Such implants can be made from bone material, man-made material, or combinations thereof. In procedures where fusion of the adjacent vertebrae is desired, bone growth material and bone growth facilitators could be provided to facilitate such fusion. Any suitable osteogenetic material or composition is contemplated for placement within or around implant 220. Such osteogenic material includes, for example, autograft, allograft, xenograft, demineralized bone, synthetic and natural bone graft substitutes, such as bioceramics and polymers, and osteoinductive factors. A separate carrier to hold the materials in the disc space or in the implant can also be used. These carriers can include collagen-based carriers, bioceramic materials, such as BIO-GLASS®, hydroxyapatite and calcium phosphate compositions. The carrier material can be provided in the form of a sponge, a block, folded sheet, putty, paste, graft material or other suitable form. Moreover, the osteogenetic compositions can comprise an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agent, held within a suitable carrier material.

Figure 13:
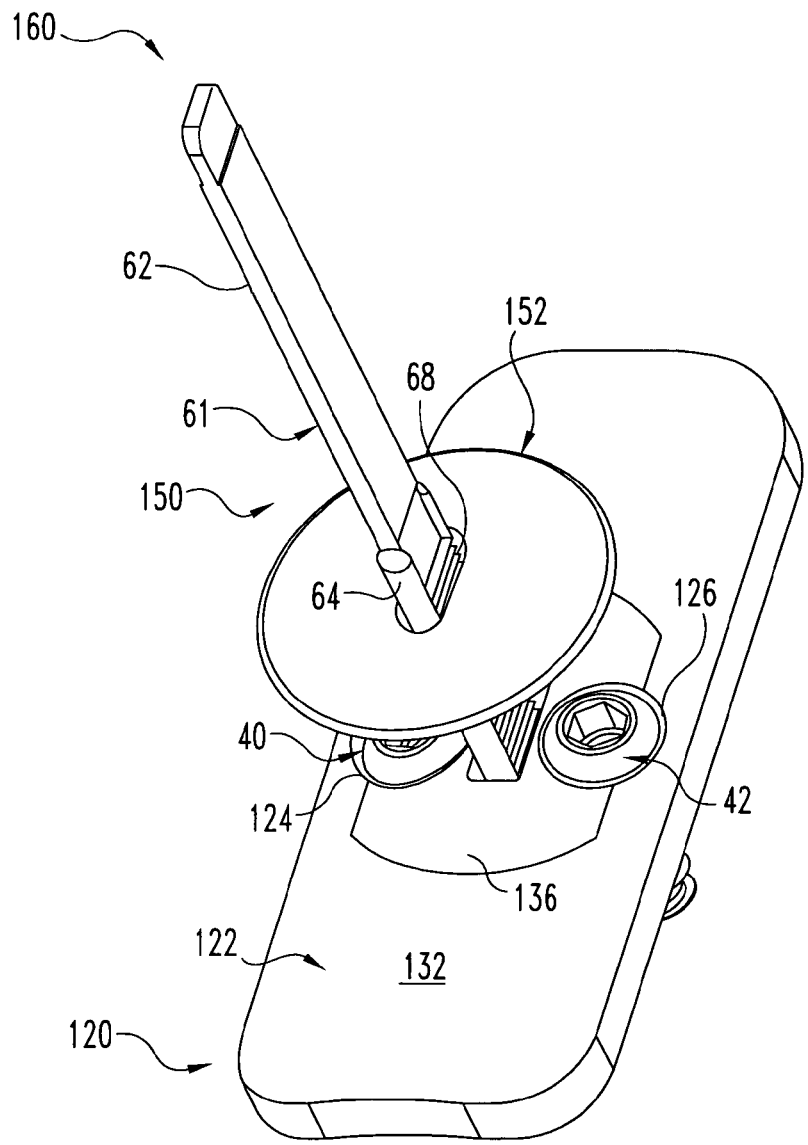
FIG. 13 is a perspective view of another embodiment plating system.

Referring to FIG. 13 there is shown a plating system 120 attachable to a bone segment that includes a plate 122 with a rectangular shape. Bone plate 122 includes holes 124, 126 for receiving bone engaging fasteners 40, 42 therethrough between a proximal surface 132 and a distal surface 134. Bone plate 122 can include distal surface 134 concavely curved about its longitudinal axis and proximal surface 132 convexly curved about its longitudinal axis. A flattened surface 136 can be formed in proximal surface 132 around holes 124, 126 to facilitate insertion of bone engaging fasteners 40, 42. It should be understood that additional holes can be provided through bone plate 122, either in isolation, in adjacent hole pairs, or three or more adjacent holes. For example, three holes could be provided in a triangular-shaped pattern in the plate, and the bone engaging fasteners therein retained by one or more retaining mechanisms. In another example, four holes could be provided in a diamond, square or rectangular shaped pattern, and the bone engaging fasteners therein retained by one or more retaining mechanisms. Additional bone engaging fasteners can be provided for any additional holes, and retaining mechanisms can be provided for contacting the bone engaging fasteners in these additional holes.

Retaining mechanism 150 can be provided with the features discussed above for retaining mechanism 50. Retaining mechanism 150 includes a retaining element 152 and an attachment portion 160. Attachment portion 160 can be similar to attachment portion 60 discussed above, and corresponding elements are designated with the same reference numeral. Attachment portion 160 includes attachment element 61 extending proximally from an abutment member 166 positionable along or against distal surface 134 of plate 122. Attachment element 61 includes proximal portion 62 and engagement portion 64.

Figure 14:
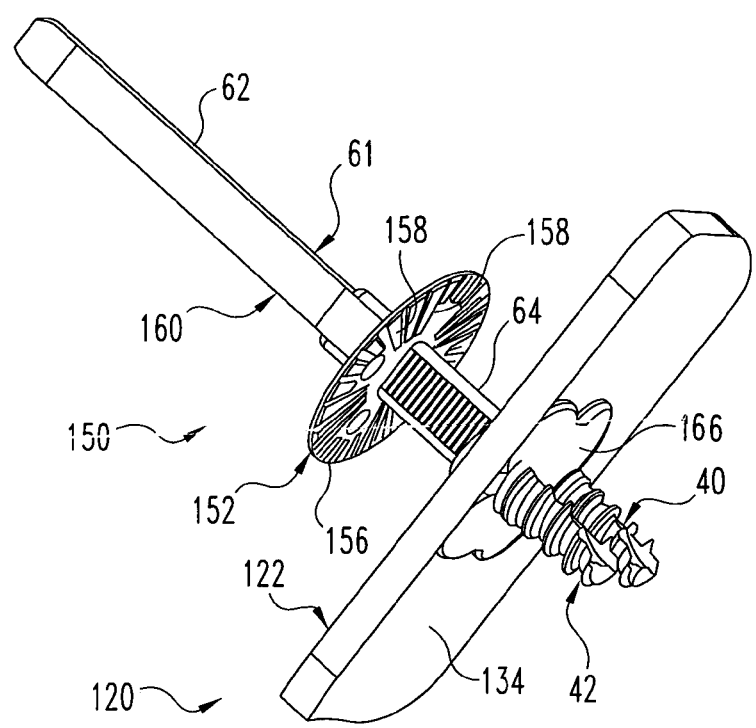
FIG. 14 is a perspective view looking toward the bottom of the plating system of FIG. 13.
Figure 15:
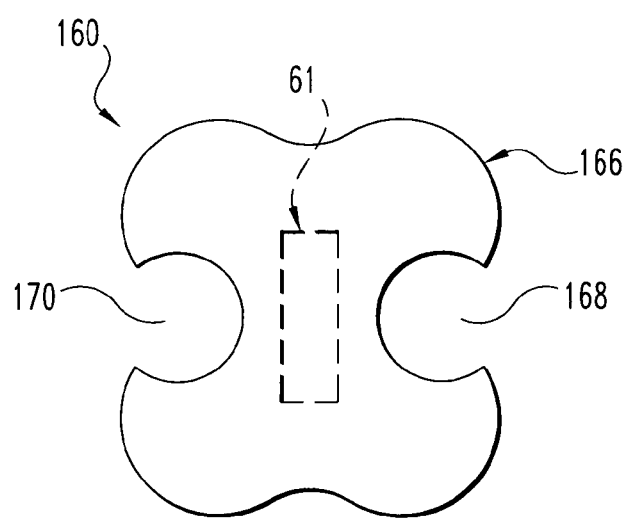
FIG. 15 is a bottom view of an attachment portion of a retaining mechanism of the plating system of FIG. 13.

As shown in FIGS. 14–15, abutment member 166 includes a first passage 168 and a second passage 170. Passages 168, 170 can be sized to receive respective ones of the bone engaging fasteners 40, 42 therethrough. The threads along the bone engaging fasteners can engage abutment member 166 to secure it relative to bone plate 122, and prevent or resist abutment member 166 from rotating relative to plate 122 before, during and/or after attachment of retaining element 152. In the illustrated embodiment, passages 168, 170 have an open side. It is also contemplated that passages 168, 170 could be completely enclosed by abutment member 166. It is further contemplated that passages 168, 170 could be formed by the bone engaging fasteners 40, 42 as each is inserted through the respective plate hole and engaged to the underlying bony segment.

Abutment member 166 can be provided with a four-leaf clover like shape as shown in the illustrated embodiment. Other shapes are also contemplated, including square, rectangular, circular, oval, polygonal or other shapes suitable to abut a distal surface of the bone plate and receive bone engaging fasteners therethrough.

Retaining mechanism 150 includes retaining element 152 for contacting one or more bone engaging fasteners positioned in the plate to engage the plate to the underlying bony segment. Retaining element 152 can have a circular shape as shown, and can also include any other suitable shape for contacting the heads of the bone engaging fasteners 40, 42, including those discussed above with respect to retaining element 52. Retaining element 152, like retaining element 52, can be sized to cover all or a portion of the heads of the bone engaging fasteners 40, 42.

Retaining element 152 can be provided with a body 156 having a plurality of protrusions or surface features 158 extending from a distal surface thereof. Surface features 158 can contact the heads of bone engaging fasteners 40, 42 to resist slippage of retaining element 152 relative thereto.

The plates discussed herein can be made from any one or combination of suitable material, including metals and metal alloys, polymers, biologic material, synthetic material, and resorbable material. It is contemplated that the retaining mechanisms can have application with other shaped and sized plates for the anterior cervical spine, and with spinal plates for other regions of the spine, including the thoracic, lumbar, and/or sacral portions of the spine. The retaining mechanisms can be employed with spinal plates adapted for attachment to other locations about the spine, including the anterior, antero-lateral, lateral, and posterior portions of the spine. It is further contemplated that retaining mechanisms can have application in bone plates other than those used in spinal surgery. It is also contemplated that a receptacle in the plate for receiving the retaining mechanisms can be positioned adjacent only one of the fastener holes, adjacent a pair of the fastener holes, or adjacent three or more fastener holes. It is further contemplated that a plate could be provided one or more fastener holes without any receptacle adjacent thereto.

Figure 16:
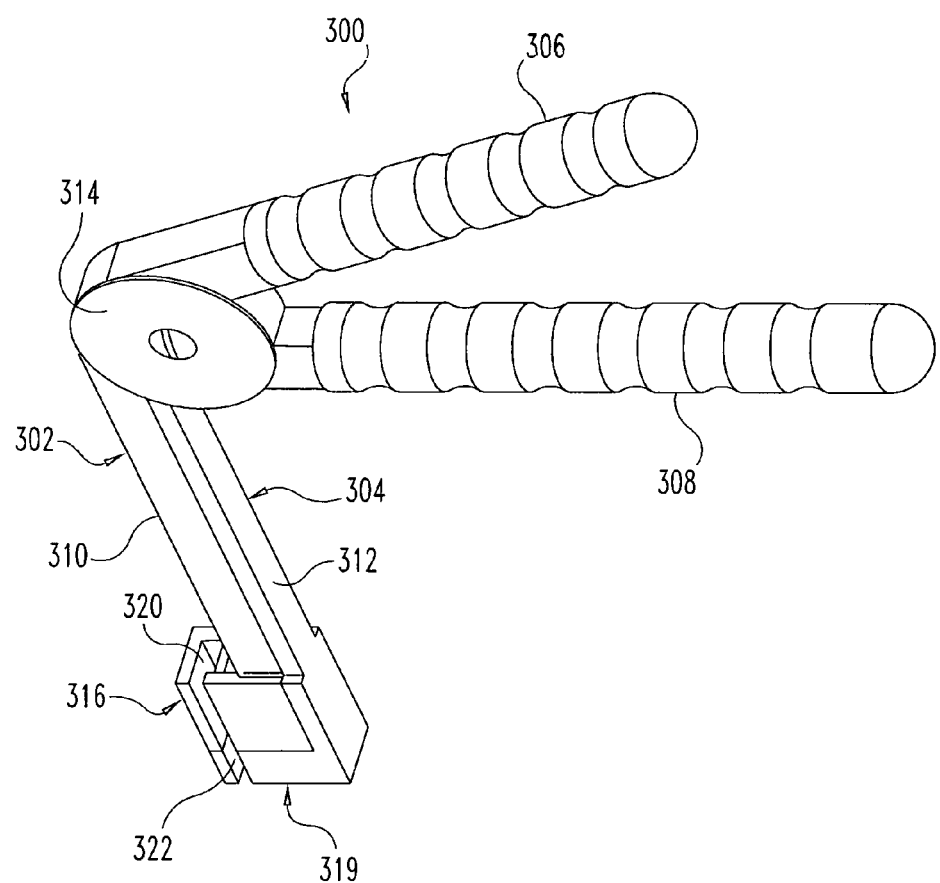
FIG. 16 is a perspective view of an instrument for engaging a retaining mechanism to a bone plate.
Figure 17:
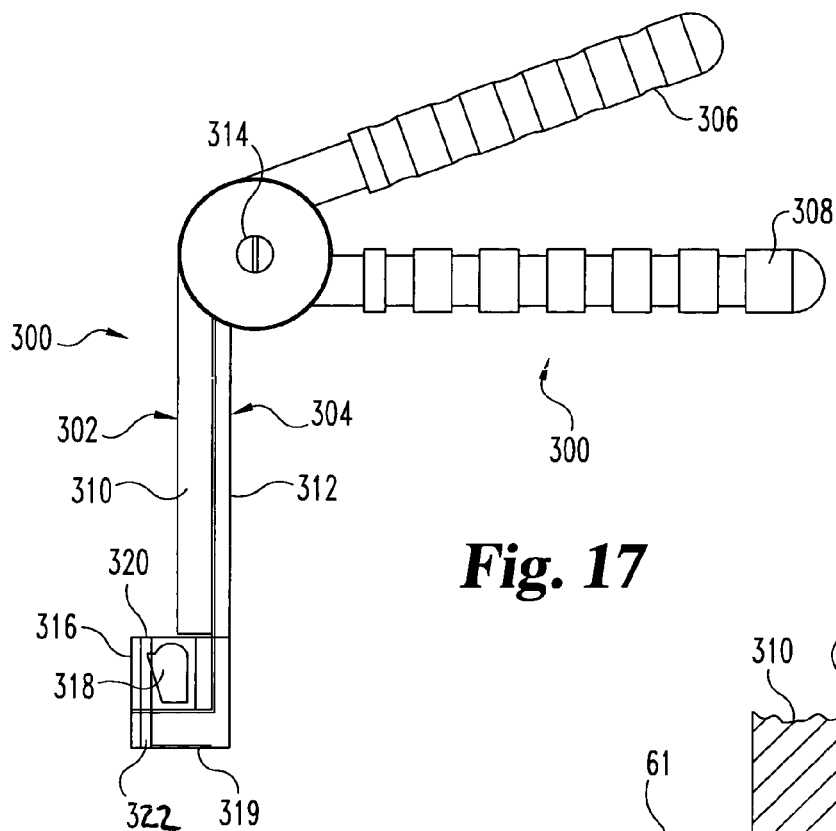
FIG. 17 is an elevation view of the instrument of FIG. 16.
Figure 18:
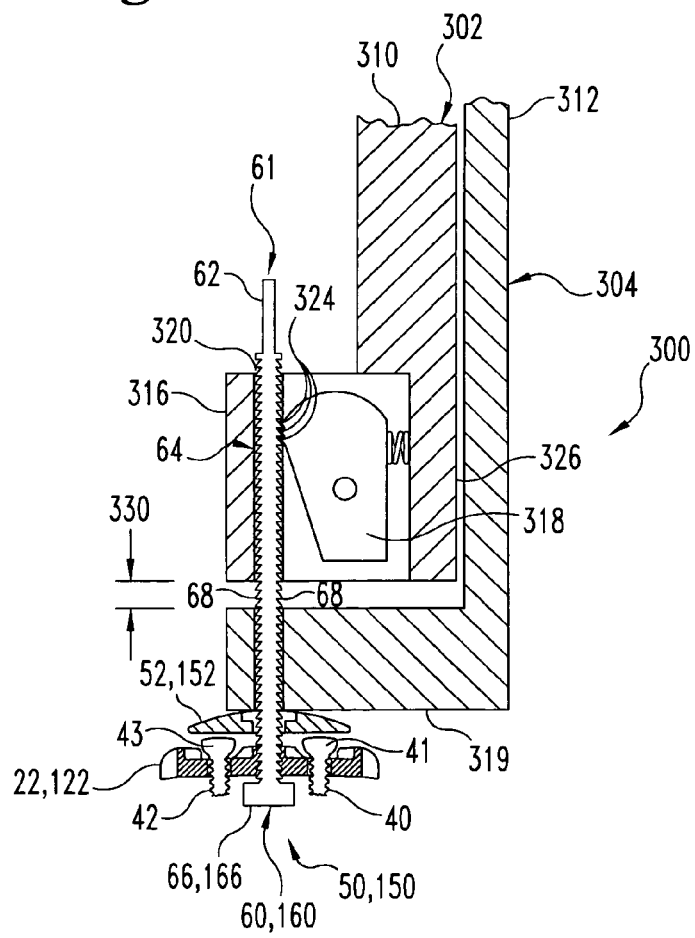
FIG. 18 is a section view of a distal portion of the instrument of FIG. 16 with the instrument engaged to a retaining mechanism attached to a bone plate.

Referring to FIGS. 16–18, there is shown an instrument 300 for positioning retaining elements 52, 152 in contact with the one or more bone engaging fasteners and/or the plate. Insertion instrument 300 includes an actuating member 302 coupled to a pushing member 304. Actuating member 302 includes a first handle 306 at a proximal end thereof, and a first shaft 310 extending distally from first handle 306. Pushing member 304 includes a second handle 308 at a proximal end thereof, and a second shaft 312 extending distally from second handle 308 along and movable relative to first shaft 310. Actuating member 302 is pivotally coupled to pushing member 304 about a hinge joint 314.

Actuating member 302 includes a housing 316 at a distal end thereof. Housing 316 includes a ratcheting member 318 therein pivotally coupled thereto. Housing 316 includes a proximal clearance channel 320 extending in the distal/proximal directions therethrough. Pushing member 304 includes a distal foot 319 extending laterally from a distal end thereof along the distal end of housing 316. Foot 319 includes a distal clearance channel 322 extending distally/proximally therethrough in alignment with proximal clearance channel 320.

Clearance channels 320, 322 can open along one side thereof so that instrument 300 can be side loaded onto the attachment element 61. It is also contemplated that channels 320, 322 could be configured to only allow top-loading of instrument 300 onto attachment element 61. The distally extending shafts 310, 312 allow instrument 300 to be inserted through retracted tissue or the like to access locations deep with the body. Handles 306, 308 can extend laterally from the shafts 310, 314 in order to not obstruct the surgeon's view of the bone plate. It is also contemplated that handles 310, 314 could extend axially from the respective shafts 310, 312.

Ratcheting member 318 can be provided with a plurality of teeth 324 therealong. As shown in the orientation of FIG. 18, ratcheting member 318 can be spring-biased in the counterclockwise direction such that teeth 324 normally extend into proximal clearance channel 320 of housing 316. When attachment element 61 is positioned in clearance channels 320, 322, teeth 324 engaged ratchet surface 68.

As shown in FIG. 18, attachment portion 60, 160 can be attached to the plate so that attachment element 61 extends proximally from the bone plate 22, 122. Retaining element 52, 152 is positioned along attachment element 61 in engagement with engagement portion 64. Proximal portion 62 and any portion of attachment element 61 extending proximally from the retaining element is placed in clearance channels 320, 322 such that foot 319 is adjacent to or in contact with the proximal side of the retaining element 52, 152. Ratcheting member 318 can pivot in the clockwise direction against the bias of spring 326 to allow attachment element 61 to be positioned in clearance channels 320, 322 in engagement with ratcheting member 318.

As handle 306 is moved toward handle 308, one or more of the teeth 324 of actuating member 302 are pulled proximally into engagement with one or more of the teeth along ratchet surface 68 of attachment element 61. This holds actuating member 302 in position relative to attachment element 61. As handle 306 is further moved toward handle 308, pushing member 304 and thus foot 319 are advanced distally from housing 316 a distance 330 along attachment element 61. Foot 319 pushes the retaining element 52, 152 distally along attachment element 61 into contact with the heads 41, 43 of the bone engaging fasteners 40, 42 and/or the proximal surface of the plate. This pushing force can resiliently deform retaining element 52, 152 and/or attachment element 61 to contact bone engaging fasteners 40, 42 at any one of a plurality of mismatched or identical positions of the heads of the bone engaging fasteners relative to plate 22, 122. As retaining element 52, 152 is pushed onto the bone plate 22, 122 attachment element 61 is tensioned, and retaining mechanism 50, 150 applies a clamping force to plate 22, 122 with abutment member 66, 166 and retaining element 52, 152.

Other instruments for axially advancing retaining elements 52, 152 along attachment element 61 of attachment portions 60, 160 are contemplated. For example, the pushing member and actuating member could be movable relative to one another by a linkage mechanism, trigger mechanism, or other coupling arrangement therebetween. Retaining elements 52, 152 could also be manually advanced along attachment element 61 into contact with the bone engaging fasteners and/or the plate.

Instrument 300 could also be configured to allow the portion of attachment element 61 extending proximally from the attached retaining element to be cut or severed while instrument 300 holds attachment element 61 in tension. For example, foot 319 could be provided with slot along a distal surface thereof to receive a cutting element to severe attachment element 61 at the proximal face of the retaining element. Instrument 300 could then retain the severed portion for removal from the patient.

While the invention has been illustrated and described in detail in the drawings and foregoing description, the same is to be considered as illustrative and not restrictive in character. All changes and modifications that come within the spirit of the invention are desired to be protected.

What is claimed is:

1. A system, comprising:
   a bone plate having at least one hole and at least one receptacle adjacent said at least one hole;
   a bone engaging fastener positioned in said at least one hole; and
   a retaining mechanism positioned in said receptacle and including a retaining element in contact with at least one of said bone plate and said at least one bone engaging fastener, said retaining mechanism including an abutment member in contact with a distal surface of said bone plate and coupled to said retaining element, wherein said retaining element and said abutment member are movable toward one another to apply a clamping force to said bone plate.

2. The system of claim 1, wherein said clamping force is applied to said bone engaging fastener.

3. The system of claim 1, wherein said retaining mechanism includes an attachment element extending proximally from said abutment member through said bone plate.

4. The system of claim 3, further comprising an attachment instrument engageable to said attachment element and operable to move said retaining element distally along said attachment element toward said bone plate.

5. The system of claim 3, wherein said retaining element includes a central opening through which said attachment element extends.

6. The system of claim 5, wherein said attachment element includes a ratchet surface formed therealong and said retaining element includes at least one locking member extending into said central opening in engagement with said ratchet surface.

7. The system of claim 6, wherein when engaged said locking member and said ratchet surface prevent proximal movement of said retaining element relative to said attachment element and permit distal movement of said retaining element relative to said attachment element.

8. The system of claim 3, wherein said attachment element is severable to remove a portion thereof extending proximally from said retaining element.

9. A system, comprising:
   a bone plate having at least one hole therethrough and at least one receptacle adjacent said at least one hole;
   a bone engaging fastener positioned in said hole; and
   a retaining mechanism in said receptacle including a retaining element axially loadable onto said bone plate in contact with said bone engaging fastener, said retaining element being resiliently deformable in response to movement of said at least one bone engaging fastener relative to said bone plate to maintain contact between said retaining element and said bone engaging fastener, wherein said retaining mechanism includes an attachment portion attached to said bone plate, said attachment portion including an attachment element engaged to said retaining element, said attachment element being resiliently deformable relative to said bone plate to maintain said retaining element in contact with said at least one bone engaging fastener.

10. The system of claim 9, further comprising an implant.

11. The system of claim 10, wherein the implant includes bone growth material.

12. The system of claim 9, wherein said bone plate is an anterior cervical plate.

13. A system, comprising:
    a bone plate having at least two adjacent holes therethrough and at least one receptacle adjacent said at least two holes;
    a bone engaging fastener positioned in each hole; and
    a retaining mechanism positioned in said receptacle, said retaining mechanism including an attachment portion attachable to said bone plate and a retaining element engaged to said attachment portion, said attachment portion being resiliently deformable to assume any one of a plurality of orientations relative to said bone plate wherein said retaining element maintains contact with each of said bone engaging fasteners.

14. The system of claim 13, wherein said retaining element is resiliently deformable.

15. The system of claim 13, wherein said attachment portion includes an abutment member at a distal end thereof in contact with a distal surface of said bone plate.

16. The system of claim 13, wherein said attachment portion includes an attachment element extending through said plate and engaged to said retaining element, said attachment element including a ratchet surface therealong and said retaining element including at least one locking member engageable with said ratchet surface.

17. The system of claim 16, wherein said locking member and said ratchet surface engage with one another to prevent proximal movement of said retaining element relative to said attachment element and permit distal movement of said retaining element relative to said attachment element.

18. The system of claim 16, wherein said attachment element is severable to remove a portion thereof extending proximally from said retaining element.

* * * * *